(12) United States Patent
Cole et al.

(10) Patent No.: US 8,269,972 B2
(45) Date of Patent: Sep. 18, 2012

(54) BEAM INTENSITY DETECTION IN A CAVITY RING DOWN SENSOR

(75) Inventors: Barrett E. Cole, Bloomington, MN (US); Terry Marta, White Bear Lake, MN (US)

(73) Assignee: Honeywell International Inc., Morristown, NJ (US)

( * ) Notice: Subject to any disclaimer, the term of this patent is extended or adjusted under 35 U.S.C. 154(b) by 260 days.

(21) Appl. No.: 12/826,095

(22) Filed: Jun. 29, 2010

(65) Prior Publication Data

US 2011/0317165 A1 Dec. 29, 2011

(51) Int. Cl.
*G01N 21/00* (2006.01)

(52) U.S. Cl. ......................................... 356/437

(58) Field of Classification Search .................. None
See application file for complete search history.

(56) References Cited

U.S. PATENT DOCUMENTS

| | | | |
|---|---|---|---|
| 4,051,372 A | 9/1977 | Aine | |
| 4,233,568 A | 11/1980 | Hamerdinger et al. | |
| 4,612,647 A | 9/1986 | Norvell | |
| 4,614,961 A | 9/1986 | Khan et al. | |
| 4,672,624 A | 6/1987 | Ford | |
| 4,732,480 A | 3/1988 | Fortunato et al. | |
| 4,795,258 A | 1/1989 | Martin | |
| 4,870,224 A | 9/1989 | Smith et al. | |
| 4,973,131 A | 11/1990 | Carnes | |
| 5,022,745 A | 6/1991 | Zayhowski et al. | |
| 5,040,895 A | 8/1991 | Laurent et al. | |
| 5,135,304 A | 8/1992 | Miles et al. | |
| 5,146,465 A | 9/1992 | Khan et al. | |
| 5,278,435 A | 1/1994 | Van Hove et al. | |
| 5,311,280 A | 5/1994 | Koper et al. | |
| 5,359,414 A * | 10/1994 | Howard et al. | ............... 356/468 |
| 5,408,319 A | 4/1995 | Halbout et al. | |
| 5,418,868 A | 5/1995 | Cohen et al. | |

(Continued)

FOREIGN PATENT DOCUMENTS

DE 3311808 10/1984

(Continued)

OTHER PUBLICATIONS

Bernstein et al., "Development of a Miniature Silicon PhotoAcoustic Gas Sensor," Presented at Opto 96, Leipzig, Germany, 6 pages, Sep. 26-29, 1999.

(Continued)

*Primary Examiner* — Tu Nguyen
(74) *Attorney, Agent, or Firm* — Seager Tufte & Wickhem LLC

(57) ABSTRACT

A cavity ring down gas sensor may include a radiation source emits an input beam of light having a wavelength corresponding to an absorption line of a gas to be detected. The input beam of light is coupled into an optical cavity to amplify an internal beam of light that is reflected about the optical cavity. An optical element is disposed in the optical cavity at an angle close to, but not at, the Brewster's angle to reflect a relatively small portion of the internal beam of light to a detector. When a specified light intensity is reached in the optical cavity, the input beam of light may be prevented from entering the optical cavity, and a cavity ring down time decay may be measured. The cavity ring down time decay may be related to the gas concentration of a gas to be detected in the optical cavity.

20 Claims, 3 Drawing Sheets

U.S. PATENT DOCUMENTS

| | | | |
|---|---|---|---|
| 5,430,543 A * | 7/1995 | Howard | 356/468 |
| 5,450,053 A | 9/1995 | Wood | |
| 5,468,910 A | 11/1995 | Knapp et al. | |
| 5,512,750 A | 4/1996 | Yanka et al. | |
| 5,528,040 A | 6/1996 | Lehmann | |
| 5,544,186 A | 8/1996 | Sauer et al. | |
| 5,550,373 A | 8/1996 | Cole et al. | |
| 5,629,951 A | 5/1997 | Chang-Hasnain et al. | |
| 5,677,538 A | 10/1997 | Moustakas et al. | |
| 5,679,965 A | 10/1997 | Schetzina | |
| 5,723,706 A | 3/1998 | Brasier et al. | |
| 5,739,554 A | 4/1998 | Edmond et al. | |
| 5,797,490 A | 8/1998 | Fujii et al. | |
| 5,815,277 A | 9/1998 | Zare et al. | |
| 5,832,017 A | 11/1998 | Ramdani et al. | |
| 5,834,331 A | 11/1998 | Razeghi | |
| 5,835,231 A | 11/1998 | Pipino | |
| 5,847,397 A | 12/1998 | Moustakas | |
| 5,869,896 A | 2/1999 | Baker et al. | |
| 5,900,650 A | 5/1999 | Nitta | |
| 5,909,280 A | 6/1999 | Zavracky | |
| 5,912,740 A | 6/1999 | Zare et al. | |
| 5,915,051 A | 6/1999 | Damask et al. | |
| 5,933,245 A | 8/1999 | Wood et al. | |
| 5,933,565 A | 8/1999 | Diebold | |
| 5,960,025 A | 9/1999 | Thorland et al. | |
| 5,982,788 A | 11/1999 | Hemmati | |
| 6,040,895 A | 3/2000 | Haas | |
| 6,080,988 A | 6/2000 | Ishizuya et al. | |
| 6,084,682 A | 7/2000 | Zare et al. | |
| 6,091,504 A | 7/2000 | Walker et al. | |
| 6,115,122 A | 9/2000 | Bao et al. | |
| 6,122,416 A | 9/2000 | Ooba et al. | |
| 6,147,756 A | 11/2000 | Zavracky et al. | |
| 6,208,798 B1 | 3/2001 | Morozov et al. | |
| 6,233,052 B1 | 5/2001 | Zare et al. | |
| 6,275,296 B1 | 8/2001 | Numai | |
| 6,287,940 B1 | 9/2001 | Cole et al. | |
| 6,295,130 B1 | 9/2001 | Sun et al. | |
| 6,296,799 B1 | 10/2001 | Sato et al. | |
| 6,310,904 B1 | 10/2001 | Thorland et al. | |
| 6,324,192 B1 | 11/2001 | Tayebati | |
| 6,335,669 B1 | 1/2002 | Miyazaki et al. | |
| 6,377,350 B1 | 4/2002 | Paldus et al. | |
| 6,380,531 B1 | 4/2002 | Sugihwo et al. | |
| 6,384,953 B1 | 5/2002 | Russell et al. | |
| 6,393,894 B1 | 5/2002 | Bonne et al. | |
| 6,404,648 B1 | 6/2002 | Slupe et al. | |
| 6,406,578 B1 | 6/2002 | Schober et al. | |
| 6,421,127 B1 | 7/2002 | McAndrew et al. | |
| 6,424,419 B1 | 7/2002 | Tazartes et al. | |
| 6,438,149 B1 | 8/2002 | Tayebati et al. | |
| 6,452,680 B1 | 9/2002 | Paldus et al. | |
| 6,483,130 B1 | 11/2002 | Yang et al. | |
| 6,483,149 B1 | 11/2002 | Mosher et al. | |
| 6,490,034 B1 | 12/2002 | Woias et al. | |
| 6,492,726 B1 | 12/2002 | Quek et al. | |
| 6,507,107 B2 | 1/2003 | Vaiyapuri | |
| 6,535,327 B1 | 3/2003 | Vodopyanov | |
| 6,545,739 B1 | 4/2003 | Matsumoto et al. | |
| 6,583,917 B2 | 6/2003 | Melloni et al. | |
| 6,584,126 B2 | 6/2003 | Wang et al. | |
| 6,590,710 B2 | 7/2003 | Hara et al. | |
| 6,594,059 B2 | 7/2003 | Flanders | |
| 6,597,713 B2 | 7/2003 | Ouchi | |
| 6,608,711 B2 | 8/2003 | Flanders et al. | |
| 6,627,983 B2 | 9/2003 | Tu et al. | |
| 6,658,034 B2 | 12/2003 | Garnache et al. | |
| 6,670,559 B2 | 12/2003 | Centola et al. | |
| 6,670,599 B2 | 12/2003 | Wagner et al. | |
| 6,728,286 B2 | 4/2004 | Thorland et al. | |
| 6,741,381 B1 | 5/2004 | Levenson et al. | |
| 6,784,946 B1 | 8/2004 | Schroter et al. | |
| 6,792,010 B2 | 9/2004 | Koulikov et al. | |
| 6,816,636 B2 | 11/2004 | Cole et al. | |
| 6,836,501 B2 | 12/2004 | Cox et al. | |
| 6,859,284 B2 | 2/2005 | Rella et al. | |
| 6,865,198 B2 | 3/2005 | Taubman | |
| 6,879,014 B2 | 4/2005 | Wagner et al. | |
| 6,959,023 B1 | 10/2005 | Xie et al. | |
| 6,959,024 B2 | 10/2005 | Paldus et al. | |
| 6,967,976 B2 | 11/2005 | Xie et al. | |
| 6,970,484 B2 | 11/2005 | Paldus et al. | |
| 6,985,281 B2 | 1/2006 | Wagner et al. | |
| 7,002,697 B2 | 2/2006 | Domash et al. | |
| 7,012,696 B2 | 3/2006 | Orr et al. | |
| 7,015,457 B2 | 3/2006 | Cole et al. | |
| 7,035,298 B2 | 4/2006 | Vodopyanov et al. | |
| 7,046,362 B2 | 5/2006 | Lehmann et al. | |
| 7,049,004 B2 | 5/2006 | Domash et al. | |
| 7,050,170 B2 | 5/2006 | Chilese et al. | |
| 7,064,836 B2 | 6/2006 | Bechtel et al. | |
| 7,089,781 B2 | 8/2006 | Petrovic et al. | |
| 7,101,431 B2 | 9/2006 | Miner | |
| 7,106,763 B2 | 9/2006 | Tan et al. | |
| 7,113,256 B2 | 9/2006 | Butler et al. | |
| 7,113,286 B2 | 9/2006 | Yan | |
| 7,116,423 B2 | 10/2006 | Paldus et al. | |
| 7,145,165 B2 | 12/2006 | Cox et al. | |
| 7,147,165 B2 | 12/2006 | Mongin et al. | |
| 7,147,695 B2 | 12/2006 | Mitra | |
| 7,154,595 B2 | 12/2006 | Paldus et al. | |
| 7,173,754 B2 | 2/2007 | Vodopyanov et al. | |
| 7,221,827 B2 | 5/2007 | Domash et al. | |
| 7,259,856 B2 | 8/2007 | Kachanov et al. | |
| 7,263,871 B2 | 9/2007 | Selker et al. | |
| 7,265,842 B2 | 9/2007 | Paldus et al. | |
| 7,304,799 B2 | 12/2007 | Ma et al. | |
| 7,352,464 B2 | 4/2008 | Chen et al. | |
| 7,369,242 B2 | 5/2008 | Cole et al. | |
| 7,420,686 B2 | 9/2008 | Tan | |
| 7,535,573 B2 | 5/2009 | Kachanov et al. | |
| 7,586,114 B2 | 9/2009 | Cole et al. | |
| 7,612,885 B2 | 11/2009 | Cole et al. | |
| 7,649,189 B2 | 1/2010 | Cole | |
| 7,656,532 B2 | 2/2010 | Cole | |
| 7,663,756 B2 | 2/2010 | Cole | |
| 2002/0017452 A1 | 2/2002 | Zimmermann et al. | |
| 2002/0191268 A1 | 12/2002 | Seeser et al. | |
| 2004/0234198 A1 | 11/2004 | Wagner et al. | |
| 2004/0255853 A1 | 12/2004 | Ma et al. | |
| 2005/0030628 A1 | 2/2005 | Wagner et al. | |
| 2005/0082480 A1 | 4/2005 | Wagner et al. | |
| 2005/0105184 A1 | 5/2005 | Ma et al. | |
| 2005/0254056 A1 | 11/2005 | Kachanov et al. | |
| 2007/0133001 A1 | 6/2007 | Cox et al. | |
| 2007/0146720 A1 | 6/2007 | Cox et al. | |
| 2007/0195434 A1 | 8/2007 | Koulikov et al. | |
| 2008/0137089 A1 | 6/2008 | Tan | |
| 2009/0113988 A1 | 5/2009 | Koulikov | |
| 2009/0185175 A1 | 7/2009 | Cole et al. | |
| 2009/0323055 A1 | 12/2009 | Cole et al. | |
| 2010/0027012 A1 | 2/2010 | Fritz et al. | |

FOREIGN PATENT DOCUMENTS

| | | |
|---|---|---|
| DE | 19635421 | 12/1997 |
| EP | 0177918 | 3/1991 |
| EP | 0667548 | 8/1995 |
| EP | 1069658 | 1/2001 |
| EP | 1070943 | 1/2001 |
| EP | 1847825 | 10/2007 |
| EP | 1061618 | 11/2007 |
| JP | 03252172 | 11/1991 |
| JP | 05095130 | 4/1993 |
| JP | 7288334 | 10/1995 |
| KR | 1020060087792 | 8/2006 |
| WO | 9326049 | 12/1993 |
| WO | 9942875 | 8/1999 |
| WO | 2004068123 | 8/2004 |
| WO | 2006000120 | 1/2006 |

OTHER PUBLICATIONS

Brown, et al., "Visible-Blind UV Digital Camera Based on a 32*32 Array of GAN/AIGAN P-I-N Photodiodes," MRS Internet Journal of Nitride Semiconductor Research, vol. 451, pp., 1-10, Sep. 1999.

Campargue et al., "Measurement of SiH2 Density in a Discharge by Intracavity Laser Absorption Spectroscopy and CW Cavity Ring-Down Spectroscopy," Journal of Physics D. Applied Physics, vol. 31, No. 10 pp. 1168-1175, May 21, 1998.

Chitica et al., "Monolithic InP-Based Tunable Filter with 10-nm Bandwidth for Optical Data Interconnects in the 1550-nm Band," IEEE Photonics Technology Letters, vol. 11, No. 5, pp. 584-586, May 1999.

Chou et al., "Diode-Laser Measurements of He-, Ar-, and N2-Broadened HF Lineshapes in the First Overtone Band," Journal of Molecular Spectroscopy 196, pp. 70-76, 1999.

Chung et al., "Design and Fabrication of 10×10 Micro-Spatial Light Modulator Array for Phase and Amplitude Modulation," Sensors and Actuators, vol. 78, No. 1, pp. 63-70, Jan. 1999.

Cole et al., "Microscopic Spectroscopy of Optical MEMS Devices," Topic 2 (Materials and Technology), Honeywell Laboratories, 2 pages, on or Around Dec. 11, 2000.

U.S. Appl. No. 12/826,095, filed Jun. 29, 2010.

Edwards, "Multiple-Traverse Absorption Cell Design," Journal of the Optical Society of America, vol. 51, No. 1, pp. 98-102, Jan. 1961.

Ferber et al., "A Miniature Silicon Photoacoustic Detector for Gas Monitoring Applications", presented at the MTEX International Conference on Sensors and Transducers, Birmingham, UK, 7 pages, Feb. 14, 2001.

Gillis et al., "Photoacoustic Spectroscopy for Quantitation of Trace Gases in Air," 2 pages, Chemical Science and Technology Laboratory National Institute of Standards and Technology, Industrial and Analytical Instruments and Services Forensics and Homeland Security, 2 pages, prior to Jul. 21, 2008.

He et al., "High-Resolution Cavity Ring-Down Absorption Spectroscopy of Nitrous Oxide and Chloroform Using a Near-Infrared CW Diode Laser," Chemical Physics Letters, vol. 289, pp. 527-534, Jun. 19, 1998.

Jerman et al., "A Miniature Fabry-Perot Interferometer with a Corrugated Silicon Diaphragm Support," Sensors and Actuators, vol. A29, No. 2, pp. 151-158, Nov. 1991.

Kurochkin et al., "Complex-Cavity Two-Mode CO2 Laser for Saturated Intracavity Absorption Spectroscopy," Optical Spectroscopy, vol. 68, No. 6, pp. 793-797, 1990.

Kurochkin et al., "Three-Mirror Cavity CO2 Laser for Intracavity Saturated-Absorption Spectroscopy," Optical Spectroscopy, vol. 65, No. 2, pp. 265-267, 1988.

Manfredi et al., "JFET Preamplifiers for Low Noise Applications in Calorimetry and Radiation Spectroscopy," Nuclear Physics B (Proc. Suppl.) 44, pp. 613-616, 1995.

O'Keefe et al., "Cavity Ring-Down Optical Spectrometer for Absorption Measurements Using Pulsed Laser Sources," Review of Scientific Instruments, 59, 11 pages, 1988.

Paul et al., "Cavity Ringdown Measures Trace Concentrations," Laser Focus World, pp. 71-80, Mar. 1997.

Pipino et al., "Evanescent Wave Cavity Ring-Down Spectroscopy with a Total-Internal-Reflection Minicavity," Rev. Sci. Instrum., vol. 68, No. 8, pp. 2978-2989, Aug. 1997.

Raymond et al., "Use of a Monolithic Dual JFET in a Low Cost, Low Noise, Charge-Sensitive Preamplifier for Semiconductor Radiation Detectors," Phys. Med. Biol., vol. 33, No. 3, pp. 367-372, 1988.

Richman et al., "Continuously Tunable, Single-Longitudinal-Mode, Pulsed Mid-Infrared Optical Parametric Oscillator Based on Periodically Poled Lithium Niobate," Optical Society of America, vol. 17, No. 7, pp. 1233-1239, Jul. 2000.

Sadeghi et al., "Cavity Ring Down Spectroscopy Applied to Plasma Diagnostics," Proc. Int. Symp. Laser-aided Plasma Diagnostics Lake Tahoe, CA, 8 pages, Sep. 1999.

Scherer et al., "Infrared Cavity Ringdown Laser Absorption Spectroscopy (IR-CRLAS) in Low Pressure Flames," Applied Physics B., vol. 64, pp. 699-705, 1997.

Schiwon et al., "Terahertz Cavity-Enhanced Attenuated Total Reflection Spectroscopy," Applied Physics Letters, vol. 86, 2005.

Schweber, "An Old Communications Problem Reoccurs in Optical-Communication-System Design—How it Works: Making the Laser Diode Tunable", EDN, 3 pages, Sep. 28, 2000.

Shimizu et al., "Stark Spectroscopy by 10μ Lasers Using a Multipath Cell," Journal of Applied Physics, vol. 46, No. 1, pp. 258-259, Jan. 1975.

Siegman, Lasers, Chapter 11-13, Copyright 1986.

Smirnov et al., "Dye Lasers Using a Three-Mirror Cavity with Lamp Excitation," 4 pages, 1981.

Spence et al., "A Laser-Locked Cavity Ring-Down Spectrometer Employing an Analog Detection Scheme," Review of Scientific Instruments, vol. 71, No. 2, pp. 347-353, Feb. 2000.

Sze, "Physics of Semiconductor Devices." pp. 763-765, John Wiley & Sons, N.Y., 1982.

Tayebati et al., "Microelectromechanical Tunable Filter with Stable Half Symmetric Cavity," Electronics Letters, IEE Stevanage, GB, vol, 34, No. 20, pp. 1967-1968, Oct. 1998.

Tayebati et. al., "Widely Tunable Fabry-Perot Filters Using High Index-Contrast DBRs," Design and Manufacturing of WDM Devices, Dallas, Texas, Nov. 4-5, 1997, SPIE vol., 3234, pp. 206-218, 1998.

Yang et al., "Back-Illuminated GAN/AIGAN Heterojunction Photodiodes With High Quantum Efficiency and Low Noise," Applied Physics Letters, vol. 73, No. 8, pp. 1086-1088, XP000777678, Aug. 24, 1998.

* cited by examiner

BEAM INTENSITY DETECTION IN A CAVITY RING DOWN SENSOR

FIELD

The present disclosure relates generally to cavity ring down sensors, and more particularly, to methods and systems for detecting and/or regulating the beam intensity of cavity ring down sensors.

BACKGROUND

Gas sensors are widely used across many diverse applications including commercial, industrial, military and other applications. The sensitivity of such gas sensors can vary, and the type of gas sensor used for a particular application is often selected depending on the required sensitivity and cost. In some applications, it may be desirable to detect gas concentrations as low as a few parts per billion, or even less. Many commercially available gas sensor, such as cavity ring down gas sensors, provide an optical cavity having an internal beam of light that is pumped up to a relatively high beam intensity in order to increase the sensitivity of the sensor. Monitoring and controlling the beam intensity can have implications on the operation of such sensors.

SUMMARY

The present disclosure relates generally to gas sensors, and more particularly, to methods and systems for detecting and/or regulating the beam intensity of cavity ring down sensors. In one illustrative embodiment, a gas sensor may be provided that includes an electromagnetic radiation source (e.g. laser) configured to emit an input beam of light having a wavelength corresponding to an absorption wavelength of a gas to be detected. The gas sensor may also include an optical cavity including at least two mirrors separated by one or more optical segments, where one of the at least two mirrors couples the input beam of light into the optical cavity. The at least two mirrors may reflect an internal beam of light around the optical cavity, and the input beam of light may contribute to the internal beam of light to effectively pump up the intensity of the internal beam of light over time.

An optical element may be disposed in at least one of the optical segments of the optical cavity, and may be configured to reflect a portion of the internal beam of light to a detector. The detector may provide a signal that indicates when the internal beam of light has reached a threshold intensity. In some cases, a beam control element (e.g. an acousto-optic modulator) may be used to selectively allow the input beam of light emitted by the electromagnetic radiation source to enter the optical cavity, and to selectively prevent the input beam of light from entering the optical cavity. A controller may receive the signal from the detector and, when the controller determines that the intensity of the internal beam of light in the optical cavity has reached a threshold level, the controller may cause the beam control element to prevent the input beam of light from entering the optical cavity. Then, a cavity ring down time of the internal beam of light in the optical cavity can be determined, sometimes through a second detector. The cavity ring down time may be related to the concentration of the gas of interest in the optical cavity.

In some cases, the optical element may be positioned in one of the optical segments at an angle close to, but not at, the Brewster's angle. In some cases, the optical element may be positioned so that optical element provides a cavity loss of 10 parts per million (ppm) or less, 4 parts per million (ppm) or less, or 2 ppm or less. Also, in some cases, the optical element may be configured to have substantially no internal absorption of the internal beam of light.

An illustrative method of detecting a gas may include transmitting an input beam of light from an electromagnetic radiation source into an optical cavity, wherein the optical cavity includes at least two mirrors separated by one or more optical segments. The at least two mirrors may reflect an internal beam of light around the optical cavity, where the input beam of light has a wavelength that corresponds to an absorption line of a gas to be detected, and contributes to the internal beam of light. A portion of the internal beam of light may be reflected off an optical element in the optical cavity. Then, a measure related to the intensity of the internal beam of light in the optical cavity may be determined from the reflected portion of the internal beam of light. The input beam of light may be stopped from entering the optical cavity and contributing to the internal beam of light when the measure related to the intensity of the internal beam of light in the optical cavity indicates that the intensity of the internal beam of light in the optical cavity has reached a threshold intensity. Once the input beam of light is stopped, a cavity ring down time of the internal beam of light may be determined.

The preceding summary is provided to facilitate an understanding of some of the innovative features unique to the present disclosure and is not intended to be a full description. A full appreciation of the disclosure can be gained by taking the entire specification, claims, drawings, and abstract as a whole.

BRIEF DESCRIPTION

The disclosure may be more completely understood in consideration of the following detailed description of various illustrative embodiments of the disclosure in connection with the accompanying drawings, in which.

DESCRIPTION

Figure 1:
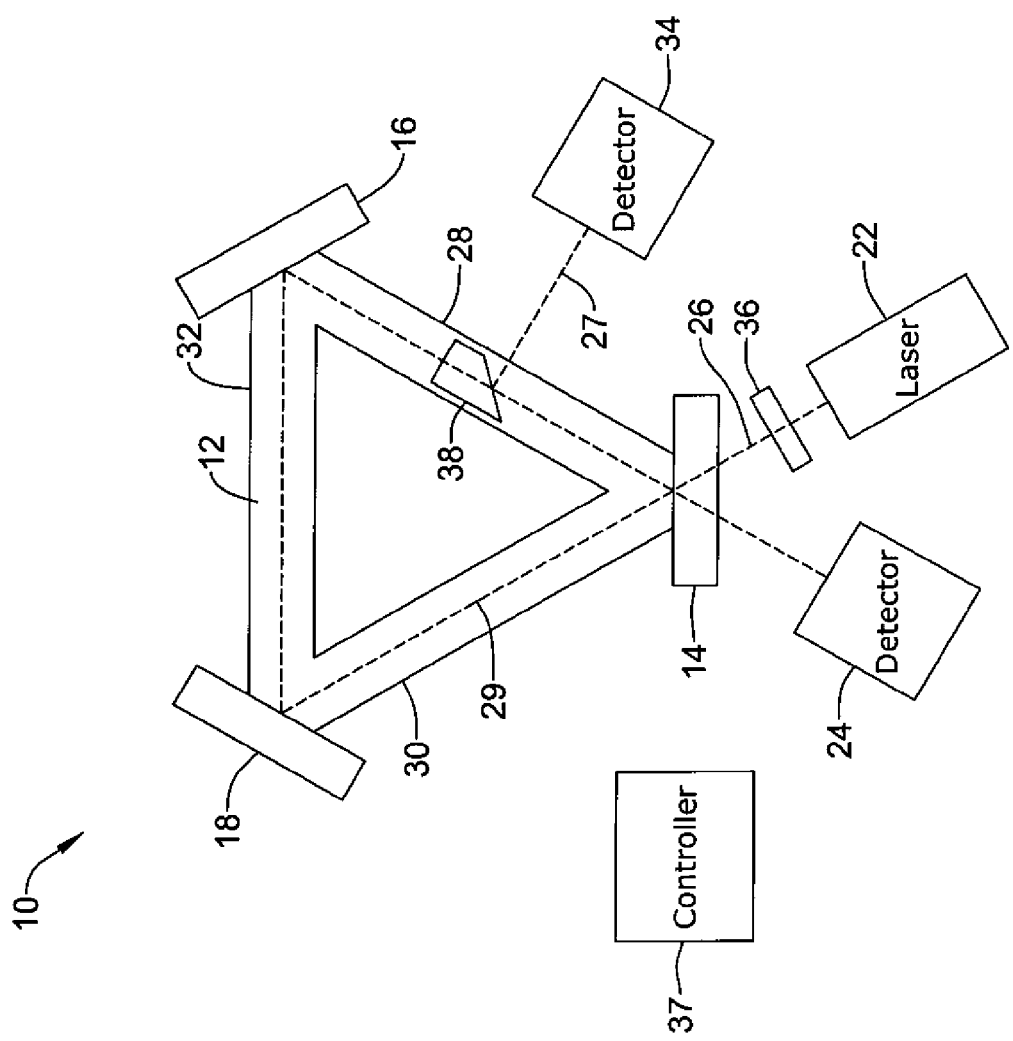
FIG. 1 is a schematic diagram of an illustrative cavity ring down gas detection system.

The following description should be read with reference to the drawings wherein like reference numerals indicate like elements throughout the several views. The detailed description and drawings show several embodiments which are meant to be illustrative of the claimed invention.

FIG. 1 is a schematic diagram of an illustrative cavity ring down gas detection system 10. The illustrative cavity ring down gas detection system 10 may provide a sensitive gas sensor that can be used to detect relatively low concentrations of gas in an environment. In some cases, the cavity ring down gas detection system 10 may be capable of accurately detecting gas concentrations as low as a few parts per billion, a few parts per trillion, or even a few parts per quadrillion or less, as desired.

In the illustrative embodiment of FIG. 1, the cavity ring down gas detection system 10 may include an electromagnetic radiation source 22, an optical cavity 12 configured to receive a gas sample, and a detector 24. The illustrative electromagnetic radiation source 22, which in some cases may be a laser, a light-emitting diode (LED) or any other suitable light source, may be configured to emit a beam of electromagnetic radiation, such as input beam of light 26. In some embodiments, input beam of light 26 may be emitted by a coherent light source such as a laser 22. In some instances, the laser 22 may be tunable to different wavelengths, which may be useful to help identify a particular gas species in the gas sample, but this is not required. When so provided, beam of light 26 of laser 22 may be tuned to a high (or other) absorption line, or wavelength close thereto, of a gas to be detected. In some cases, the laser 22 may be infrared (IR) tunable input laser that is tunable in or around the infrared band.

In some instances, the laser 22 may be a fixed wavelength (i.e. non-tunable) light source. In this case, laser 22 may be selected to have a wavelength that is close to or at a high (or other) absorption line of a gas species to be detected. Quantum cascade lasers may be suitable, but not required. Some example lasers that may be suitable include, for example, lasers available from New Focus™, such as the Velocity Product line, Telecom, or Daylight Solutions, such as a 4.5 micron laser model number TLS-21045 or a Chiller Model 1001 having a model number TLS-21045. The wavelength of the laser to be used depends on the absorption spectra of the gas sample. While lasers are used in one example, this is not meant to be limiting, and it is contemplated that any suitable electromagnetic radiation source may be used, as desired.

In the illustrative embodiment of FIG. 1, the optical cavity 12 has three linear optical segments 28, 30, and 32 arranged to define a triangular-shaped optical path for the optical cavity 12. In this illustrative embodiment, the optical cavity 12 includes three mirrors 14, 16, and 18 arranged so as to permit an internal beam of light 29 to travel in a continuous path around the optical cavity 12. As illustrated, mirrors 14, 16, and 18 are disposed in each of three corners of the optical cavity 12. As shown, mirror 14 intersects optical linear segment 28 and optical linear segment 30, mirror 16 intersects optical linear segment 30 and optical linear segment 32, and mirror 18 intersects optical linear segment 32 and optical linear segment 28 of optical cavity 12. While three mirrors are shown in the illustrative embodiment of FIG. 1, it is contemplated that more or less mirrors may be used, as desired. For example, it is contemplated that two mirrors that causes light beams to travel back and forth between the two mirrors can be used, if desired.

In some cases, mirrors 14, 16 and 18 may all be passive mirrors. In some instances, mirrors 14 and 16 may be passive mirrors, and mirror 18 may be an active mirror. In yet other instances, it is contemplated that mirror 16 may be an active mirror and mirror 18 may be a passive mirror or mirror 16 and 18 may be active mirrors, if desired. In some cases, active mirror 18 may be deformable or otherwise actuatable, and passive mirrors 14 and 16 may be non-deformable. For example, passive mirrors 14 and 16 may be dielectric mirrors. In one illustrative embodiment, dielectric mirrors 14 and 16 may be configured to have a relatively high reflectivity on the internal surface and to be at least partially transparent on the external surface. The relatively high reflectivity on the internal surface of dielectric mirror 14 and 16 may help to reflect light within the optical cavity 12 to reduce loss. The at least partial transparency on the external surface of, for example, mirror 14, may help input beam of light 26 pass through mirror 14 to enter the optical cavity 12 and to contribute to the internal beam of light 29 reflected around the optical cavity 12.

When so provided, active mirror 18 may be mechanically and/or electrically deformable or otherwise actuatable so as to move the optical cavity 12 in and out of resonance conditions with two or more absorption lines. In one illustrative embodiment, a first resonance condition may correspond to a wavelength for a high (or other) absorption line of a gas to be detected, and a second resonance condition may correspond to a wavelength for a different absorption line of the same gas to be detected, or of an absorption line of a different gas to be detected. A tunable electromagnetic radiation source 22 may be used to selectively provide wavelengths in the input beam of light 26 to correspond to the resonance conditions of the optical cavity 12.

In some cases, the active mirror 18 may be a piezoelectric mirror 18. Piezoelectric mirror 18 may be configured to deform when an electrical potential is applied across a piezoelectric element of the active mirror 18. For example, an applied electrical potential may cause at least a portion of the mirror to expand and/or contract. In one example, the center of the piezoelectric mirror 18 may move in and out in response to the applied electrical potential, causing the focal length of the mirror 18 to change. In some embodiments, the electrical potential may oscillate, causing the piezoelectric mirror 18 to deform at a frequency of the applied oscillating electrical potential. The frequency that the active mirror 18 oscillates may dictate an acoustic chopping frequency at which light pulses are periodically applied to the optical cavity 12.

In some cases, the piezoelectric mirror 18 may be configured to deform around a node position providing a resonance. The node position may be a position of the piezoelectric mirror 18 in which the optical cavity 12 may have a resonance condition for a particular wavelength of light. For example, the node position of the piezoelectric mirror 18 may correspond to the resonance condition for electromagnetic radiation source 22 at a particular absorption line of a gas to be detected. Accordingly, the oscillation of the piezoelectric mirror 18 may cause the optical cavity 12 to move in and out of the resonance conditions that correspond to two or more different absorption lines at the oscillating frequency of the piezoelectric mirror 18. In some cases, the resonance condition may occur twice for each oscillation cycle of the mirror 18, but could be more or less depending on the resonance condition of the optical cavity 12. In one example, the oscillating frequency of the piezoelectric mirror 18 may be such that each of the resonance conditions of the optical cavity 12 occur on the order of milliseconds, however, any suitable time period may be used. Similar to mirrors 14 and 16, piezoelectric mirror 18 may be configured to have a relatively high reflectivity on the internal surface to reduce loss, and in some cases, be at least partially transparent on the external surface.

In the illustrative embodiment of FIG. 1, passive mirror 14 is an entrance mirrors for the optical cavity 12, or more specifically, passive mirror 14 is the mirror in which the input beam of light 26 passes through to enter the optical cavity 12. With the optical cavity 12 is in a resonance condition for the input beam of light 26, the input beam of light 26 may be coupled into the optical cavity 12 via passive mirror 14, and may add to the internal beam of light 29. This may amplify the internal beam of light 29 in the optical cavity 12. This amplification may help increasing the sensitivity of the detection of gas in the optical cavity 12. In some cases, the amplification of the internal beam of light 29 may be on the order of 100 times to 1000 times or more relative to the amplitude of the input beam of light 26 emitted by light source 22. When the input beam of light 26 is prevented from entering the optical cavity 12, the internal beam of light 29 traveling around the optical cavity 12 is stored for a period of time, typically on the order of microseconds, but decays with a cavity ring down time decay. The cavity ring down time decay is typically dependent on the amount of absorption of the internal beam of light 29 by the gas in the optical cavity 12, which is related to the concentration of the gas in the optical cavity 12.

A detector 24 may be configured to detect the ring down time decay of the internal beam of light 29, which as discussed above, may be related to the absorption of the internal beam of light 29 by the gas in the optical cavity 12. In some cases, the detector 24 may be an optical detector that is configured to detect optical light that escapes through one of the mirrors, such as mirror 14.

In the illustrative embodiment of FIG. 1, a beam control element 36 (e.g. an acousto-optic (AO) modulator), may be associated with the electromagnetic radiation source 22 to selectively transmit the input beam of light 26 into the optical cavity 12. In some cases, an AO modulator 36 may be considered as part of the electromagnetic radiation source 22, but this is not required.

When it is determined that the intensity of the internal beam of light 29 in the optical cavity 12 is at a threshold level, the beam control element 26 (e.g. AO modulator) may cease to direct, or may otherwise prevent, the input beam of light 26 from coupling into the optical cavity 12. In some cases, the threshold intensity limit may be a predetermined, predefined, or some other specified intensity threshold. In some instances, it is contemplated that electromagnetic radiation source 22 may simply be shut off when the intensity threshold is reached in the optical cavity 12, instead of, or in addition to, utilizing a beam control element 36 as shown in FIG. 1, if desired.

In the illustrative embodiment, an optical element 38 (e.g. a partial reflector) is positioned or formed in the optical cavity 12 in one of the optical segments 28, 30, and 32. As shown, the optical element 38 is positioned in optical segment 28, but this is just one example. Optical element 38 may be positioned in optical segment 30 or optical segment 32, if desired. The optical element 38 is configured to have a transmittance of internal beam of light 29 that is close to, but not at, 100 percent, and a reflectance that is close to, but not at, zero. For example, the optical element 38 may transmit about 99.9999 percent, about 99.9998 percent, about 99.9997 percent, about 99.9996 percent, about 99.9995 percent, about 99.9994 percent, about 99.9990 percent, or any other percentage, as desired. In some cases, the optical element 38 may be configure to reflect a small portion of the internal beam of light 29 in the optical cavity 12, such, for example, 1 ppm or less, 2 ppm or less, 3 ppm or less, 4 ppm or less, 5 ppm or less, 6, ppm or less, 7 ppm or less, 8 ppm or less, 9 ppm or less, 10 ppm or less, 20 ppm or less, 40 ppm or less, or any desired amount of internal beam of light 29, as desired.

More generally, the optical element 38 may be configured to provide additional cavity loss that does not significantly affect the ring down time decay of the internal beam of light 29 in the optical cavity 12. For example, high quality optical cavities can have a cavity loss in the range of 10-100 ppm cause by, for example, light leaking out of one or more of the mirrors 14, 16, and 18, or due to other causes. An additional loss in the range of 1-10 ppm or 1-20 ppm caused by the optical element 38 reflecting part of the internal beam of light 29 out of the optical cavity 12 as shown by reflected beam of light 27 may not significantly increase the overall cavity loss. In some cases, the cavity ring down gas sensor 10 may be calibrated and/or programmed to compensate for the reflected beam of light 27, which in some cases, may allow for a higher ppm to be reflected.

The transmittance and reflectance of optical element 38 is determined, at least in part, on the angle of the optical element 38 relative to the internal beam of light 29. In one embodiment, the optical element 38 may be precisely oriented just off of the Brewster's angle, which may be determined according to the material of the optical element 38. In one example, for Infrasil™ and at a wavelength of 1.5 micrometers, the optical element 38 may be oriented at an angle of about 55.3 degrees relative to the internal beam of light 29, which is described in further detail in with regards to FIG. 3. In this example, the optical element 38 may be oriented at 0.01 degrees off of the Brewster angle. However, in other examples, the optical element may be oriented at about 0.02 degrees off of the Brewster angle, about 0.03 degrees off of the Brewster angle, about 0.04 degrees off of the Brewster angle, or any other suitable orientation relative to the Brewster angle, as desired.

In some embodiments, the optical element 38 may be machined on an internal surface of the optical cavity 12. For example, optical element 38 may be formed as a boss extending into the optical cavity 12 to intersect the internal beam of light 29. In addition or in the alternative, the optical element 38 may include a thin membrane. For example, the optical element 38 may include a thin membrane suspended over an etched, machined or otherwise formed through-hole in a substrate. In some embodiment, the optical element 38 may be configured to reduce and/or substantially eliminate any internal absorption of the internal beam of light 29. In some instances, reducing the thickness of the optical element 38 (e.g. membrane) and/or selecting a material having low internal absorption may help reduce internal cavity loss. The optical element may include a suitable material having desired transmission and reflection properties to achieve a desired reflectance of the internal beam of light 29. Example materials may include, for example, glass, $Si_3N_4$, $SiO_2$, and/or other suitable materials, as desired.

As shown in FIG. 1, a detector 34 can be positioned to detect reflected beam of light 27, as shown. As illustrated, the detector 34 may receive a small portion of the internal beam of light 29 (i.e. beam of light 27), and thus may detect a measure that is related to the intensity of the internal beam of light 29 in the optical cavity 12. Detector 34 may be configured to produce a signal that is related to the intensity of reflected light 27. In some cases, the intensity of reflected beam of light 27 may directly correlate to the intensity of the internal beam of light 29 in the optical cavity 12.

In some embodiments, a controller 37 may receive the signal from the detector 34. The controller 37 may determine when the intensity of the internal beam of light 29 in the optical cavity 12 has reached a threshold intensity level. Once the threshold intensity level is reached, the controller 37 may cause the electromagnetic radiation source 22 and/or beam control element 36 (e.g. AO modulator) to decouple, shut off, stop, or otherwise prevent the input beam of light 26 from entering the optical cavity 12. It is contemplated that the controller 37 may be as complex as a microprocessor or as simple as a trigger signal generator, depending on the application. In some instances, the controller 37 may be incorporated into the detector 34, the beam control element 36, and/or any other component, or may be a separate element such as shown in FIG. 1.

In operation, the optical cavity 12 may couple in input beam of light 26, such as via mirror 14. When the optical cavity 12 is in a resonance condition, sometimes according to the current state of the active mirror 18, the input beam of light 26 may contribute or add to the internal beam of light 29, thereby amplifying the internal beam of light 29. The internal beam of light 29 may then interact with the gas sample in the optical cavity 12. The wavelength of the internal beam of light 29 may correspond to an absorption line of a gas of interest.

A portion of the internal amplified beam of light 29 (i.e. reflected beam of light 27) may be reflected by optical element 38 to a detector 34. Due to the amplification of the internal beam of light 29 in the optical cavity 12, the reflected beam of light 27, even when on the order of ppm, may provide a sufficient signal to determine the intensity, or a measure related to the intensity, of the internal beam of light 29 in the optical cavity 12. When the detector 34 detects an intensity or measure related to the intensity of the internal beam of light 29 in the optical cavity 12 above a predetermined, predefined, or some other intensity threshold, the controller 37 may cause the electromagnetic radiation source 22 and/or a beam control element 36 to stop coupling input beam of light 26 into the optical cavity 12. Detector 24 may then be used to detect a cavity ring down time decay of the internal beam of light 29. The cavity ring down time decay may be related to the amount of absorption of the internal beam of light 29 by the gas sample, which may be related to the concentration of the gas of interest in the gas sample. In some cases, the cavity ring down time decay of the optical cavity 12 may be on the order of micro-seconds, such as, for example, 10 micro-seconds, depending on the concentration and/or degree of absorption by the gas sample.

Further, it is contemplated that in an optical cavity having two mirrors, a portion of light beam 29 (i.e. reflected beam of light 27) may be reflected by optical element 38 in both directions. In this example, both sides of optical element 38 may be may be precisely oriented just off of the Brewster's angle, or other angle, as desired.

Figure 2:
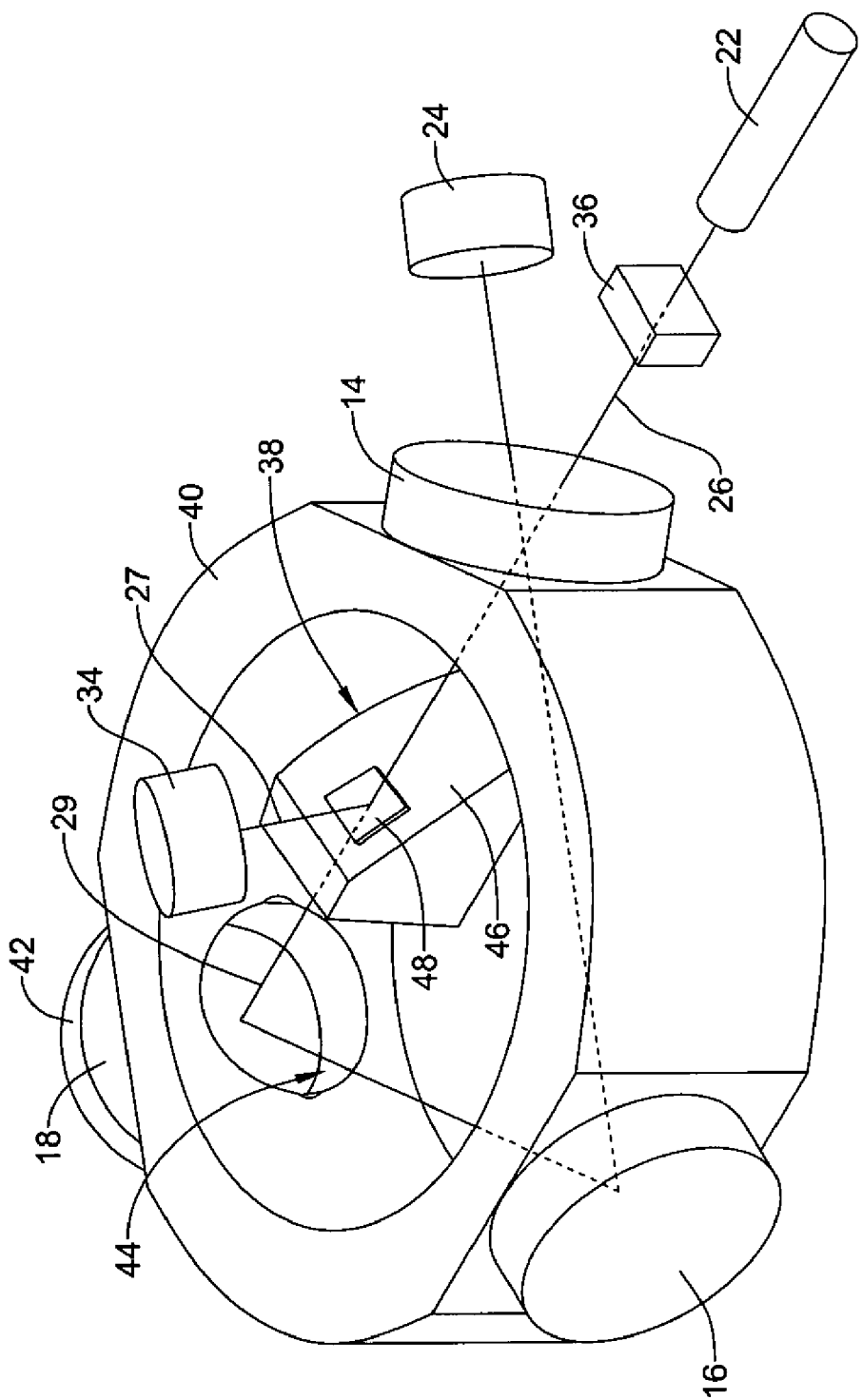
FIG. 2 is a perspective view of the illustrative cavity ring down gas detection system of FIG. 1.

FIG. 2 is a perspective view of the illustrative gas detection system 10 of FIG. 1. As illustrated, the optical cavity 12 is provided in a housing 40 defining the optical segments 28, 30, and 32. As shown, the housing 40 may define a chamber 44 forming the optical cavity 12, while in other cases, it is contemplated that the housing 40 may include individual bores defining the individual optical segments 28, 30, and 32 of the optical cavity 12, as desired. The ends of optical segments 28, 30, and 32 may intersect mirrors 14, 16, and 18, which are disposed about the side surfaces of the housing 40. As shown, and in some illustrative embodiments, mirror 18 may include an actuator 42 for actuating the position of mirror 18 to vary the resonance of the optical cavity.

In the illustrative embodiment, the optical element 38 may include a membrane 48 disposed on a substrate 46. In some cases, the substrate 46 may include a through hole (not explicitly shown, but behind the membrane 48) for passing the internal beam of light 29. In some cases, the substrate 46 may be formed integral with or formed as part of the housing 40. In some instances, although not shown in FIG. 2, the optical element 38 may be formed as a boss in one of the optical segments 28, 30, or 32 that extends to intersect with the internal beam of light 29. When provided, the membrane 48 may include a transparent or substantially transparent material, such as, for example, glass, Si3N4, SiO2, or any other suitable material, as desired. The forgoing described optical elements 38 are merely illustrative, and are not meant to be limiting in any manner. It is contemplated that any suitable optical element providing a desired transmittance and reflectance may be used, as desired.

Figure 3:
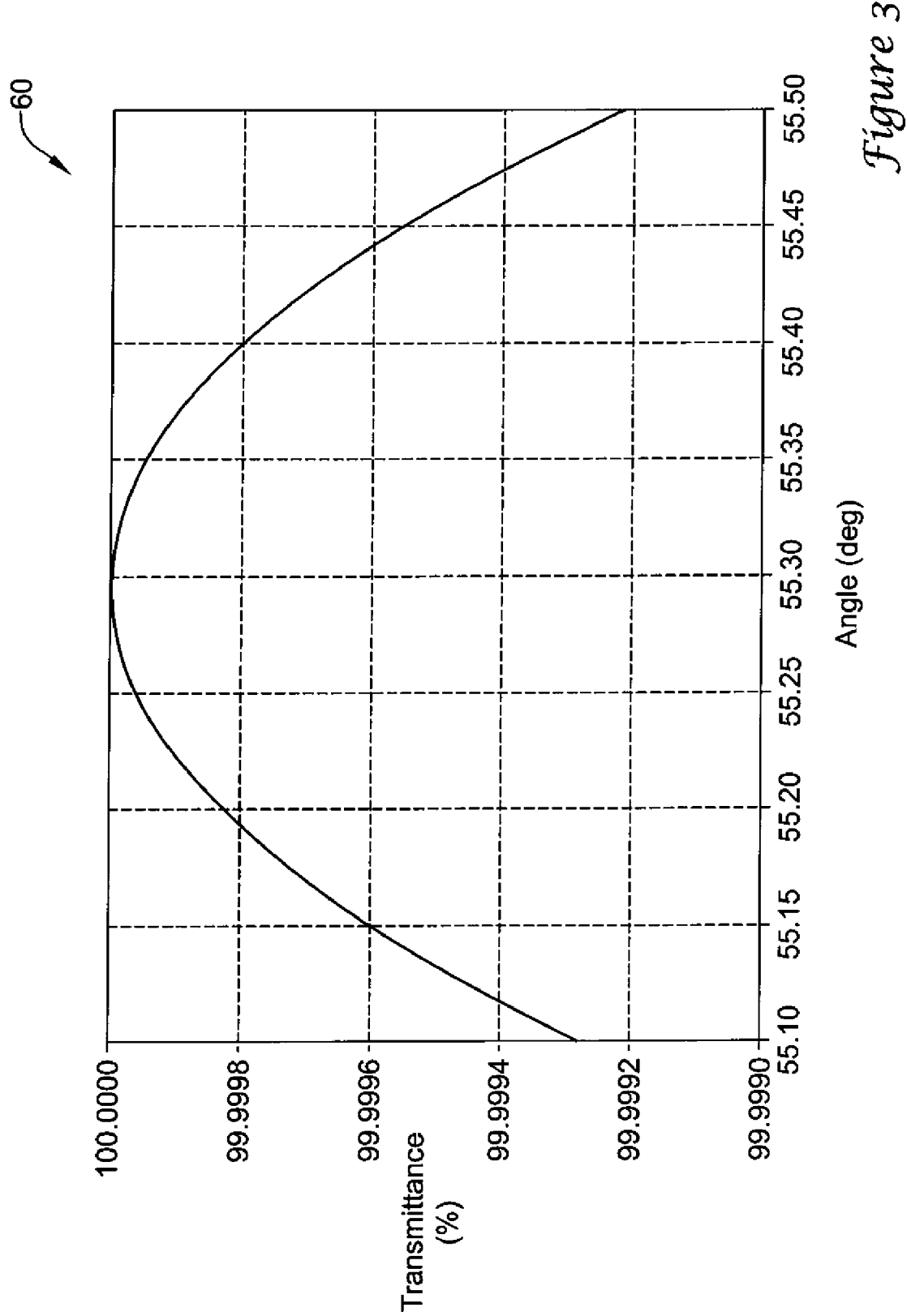
FIG. 3 is a graph showing the transmittance of a light through a material at angles close to the Brewster angle for the selected material.

FIG. 3 is a graph 60 showing the transmittance of light through a substrate material at angles close to the Brewster's angle for the material. In the illustrative embodiment, the substrate material for an optical element 38 may be Infrasil™, the wavelength of the internal beam of light may be 1.5 micrometers, and the medium surrounding the Infrasil™ material may be air. As shown in the graph, the transmittance of the Infrasil™ substrate is about 100 percent at about 55.3 degrees, or just under, which may be considered the Brewster's angle for the Infrasil™ material. The transmittance of Infrasil™ may be about 99.9998 percent at about 55.19 degrees and about 55.40 degrees. At these angles, about 2 ppm of the internal beam of light 29 may be reflected. The transmittance of Infrasil™ may be about 99.9996 at about 55.15 degrees and about 55.44 degrees. At these angles, about 4 ppm of the internal beam of light 29 is reflected. It is contemplated that the optical element 38, when including Infrasil™ or other material, can be positioned at a suitable angle such that about 1 ppm or less, 2 ppm or less, 3 ppm or less, 4 ppm or less, 5 ppm or less, 6 ppm or less, 7 ppm or less, 8 ppm or less, 9 ppm or less, 10 ppm or less, or any other desired ppm, of the internal beam of light 29 in the optical cavity 12 is reflected.

Having thus described the preferred embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respect, only illustrative. Changes may be made in details, particularly in matters of shape, size, and arrangement of parts without exceeding the scope of the disclosure. The invention's scope is, of course, defined in the language in which the appended claims are expressed.

What is claimed is:

1. A gas sensor comprising:

an electromagnetic radiation source configured to emit an input beam of light;

an optical cavity for receiving a gas to be detected, the optical cavity defined by one or more optical segments separating at least two mirrors, wherein the at least two mirrors are configured to reflect an internal beam of light through the one or more optical segments;

an optical element disposed in at least one of the one or more optical segments, wherein the optical element is configured to reflect a portion of the internal beam of light when the input beam of light emitted by the electromagnetic radiation source is selectively allowed to enter the optical cavity;

a first detector positioned to detect the portion of the internal beam of light reflected by the optical element, wherein the first detector is configured to produce a signal that is related to the intensity of the internal beam of light present in the optical cavity; and a controller coupled to the first detector, the controller is configured to receive the signal from the first detector and, when the controller determines that the intensity of the internal beam of light in the optical cavity has reached a threshold level, the controller is configured to cause the input beam of light emitted from the electromagnetic radiation source to be prevented from entering the optical cavity.

2. The gas sensor of claim 1 further comprising:

a beam control element for selectively allowing the input beam of light emitted by the electromagnetic radiation source to enter the optical cavity, and for selectively preventing the input beam of light emitted by the electromagnetic radiation source from entering the optical cavity; and wherein the controller is coupled to the beam control element, and the controller is configured to cause the input beam of light emitted from the electromagnetic radiation source to be prevented from entering the optical cavity by causing the beam control element to prevent the input beam of light emitted from the electromagnetic radiation source from entering the optical cavity.

3. The gas sensor of claim 2 further comprising a second detector, wherein the second detector is configured to detect a cavity ring down time of the internal beam of light in the optical cavity after the controller causes the beam control element to prevent the input beam of light emitted from the electromagnetic radiation source from entering the optical cavity, wherein the cavity ring down time is related to a concentration of the gas to be detected in the optical cavity.

4. The gas sensor of claim 1 wherein the optical element is positioned in at least one of the optical segments of the optical cavity, and just off the Brewster's angle of internal beam of light.

5. The gas sensor of claim 1 wherein the optical element is positioned in at least one of the optical segments of the optical cavity such that the optical element provides a cavity loss of 10 parts per million or less.

6. The gas sensor of claim 1 wherein the optical element is positioned in at least one of the optical segments of the optical cavity such that the optical element provides a cavity loss of 2 parts per million or less.

7. The gas sensor of claim 1 wherein the optical element includes a membrane disposed over a substrate including a through-hole.

8. The gas sensor of claim 1 wherein the optical element is configured to have substantially no internal absorption of the internal beam of light.

9. The gas sensor of claim 1 wherein the internal beam of light is tuned to an absorption line of the gas to be detected.

10. The gas sensor of claim 1 wherein at least one of the at least two mirrors is actuatable to move in and out of a node position that provides a resonance in the optical cavity.

11. The gas sensor of claim 10 wherein the actuatable mirror is electrically deformable.

12. The gas sensor of claim 11 wherein the electrically deformable mirror deforms around the node position according to an applied electrical potential.

13. A gas sensor comprising:
an electromagnetic radiation source configured to emit an input beam of light having a wavelength corresponding to an absorption wavelength of a gas to be detected;
an optical cavity including at least three mirrors separated by one or more optical segments, wherein the at least three mirrors are configured to reflect an internal beam of light through the one or more optical segments, wherein one of the at least three mirrors couples the input beam of light into the optical cavity;
an optical element disposed in at least one of the one or more optical segments, the optical element configured to reflect a portion of the internal beam of light in the optical cavity;
a first detector configured to detect the portion of the internal beam of light reflected by the optical element and produce a signal that is related to the intensity of the internal beam of light in the optical cavity;
a second detector for detecting a cavity ring down time of the internal beam of light in the optical cavity; and
a controller for configured to receive the signal from the first detector and, when the controller determines that the intensity of the internal beam of light in the optical cavity has reached a threshold level, the controller is configured to cause the electromagnetic radiation source to stop providing the input beam of light.

14. The gas sensor of claim 13 wherein the electromagnetic radiation source includes an acousto-optic modulator configured to selectively direct the beam of light into the optical cavity.

15. The gas sensor of claim 13 wherein the optical element is positioned in at least one of the optical segments of the optical cavity such that optical element provides a cavity loss of 4 parts per million or less.

16. The gas sensor of claim 13 wherein the optical element is positioned in at least one of the optical segments such that the optical element provides a cavity loss of 2 parts per million or less.

17. A method of detecting a gas, the method comprising:
transmitting an input beam of light from an electromagnetic radiation source into an optical cavity, wherein the optical cavity includes the at least two mirrors separated by one or more optical segments, and wherein the at least two mirrors reflect an internal beam of light around the optical cavity, the input beam of light having a wavelength that corresponds to an absorption line of a gas to be detected and contributes to the internal beam of light;
reflecting a portion of the internal beam of light off an optical element in the optical cavity;
determining a measure related to the intensity of the internal beam of light in the optical cavity from the reflected portion of the internal beam of light; and
stopping the input beam of light from entering the optical cavity and contributing to the internal beam of light when the measure related to the intensity of the internal beam of light in the optical cavity indicates that the intensity of the internal beam of light in the optical cavity has reached a threshold intensity.

18. The method of claim 17 further comprising detecting a cavity ring down time of the internal beam of light in the optical cavity after the stopping step to determine a measure related to a concentration of the gas to be detected in the optical cavity.

19. The gas sensor of claim 17 wherein the optical element is positioned in at least one of the optical segments of the optical cavity such that the optical element provides a cavity loss of 4 parts per million or less.

20. The gas sensor of claim 17 wherein the optical element is positioned in at least one of the optical segments of the optical cavity such that the optical element provides a cavity loss of 2 parts per million or less.

* * * * *